(12) United States Patent
Martin

(10) Patent No.: US 7,763,850 B2
(45) Date of Patent: *Jul. 27, 2010

(54) METHOD AND DEVICE FOR THE REAL-TIME MEASUREMENT OF THE CONSUMPTION OF OIL FROM AN ENGINE OIL SEPARATION SYSTEM, USING RADIOACTIVE TRACERS

(75) Inventor: François Martin, Lyons (FR)

(73) Assignees: Total Raffinage Marketing, Puteaux (FR); Delta Services Industriels S.P.R.L., Froyennes (BE)

( * ) Notice: Subject to any disclaimer, the term of this patent is extended or adjusted under 35 U.S.C. 154(b) by 894 days.

This patent is subject to a terminal disclaimer.

(21) Appl. No.: 10/591,397

(22) PCT Filed: Mar. 11, 2005

(86) PCT No.: PCT/FR2005/000590

§ 371 (c)(1),
(2), (4) Date: Oct. 27, 2006

(87) PCT Pub. No.: WO2005/088085

PCT Pub. Date: Sep. 22, 2005

(65) Prior Publication Data

US 2008/0156083 A1 Jul. 3, 2008

(30) Foreign Application Priority Data

Mar. 11, 2004 (FR) .................................. 04 02541

(51) Int. Cl.
*G01T 7/02* (2006.01)
*G01T 1/16* (2006.01)
(52) U.S. Cl. ........................ 250/303; 250/301; 250/302
(58) Field of Classification Search .................. 250/259, 250/260, 261, 301, 302, 303, 458.1, 459.1; 73/861.07, 861; 324/451, 452, 453, 459, 324/461
See application file for complete search history.

(56) References Cited

U.S. PATENT DOCUMENTS 2,939,011 A 5/1960 Bisso et al.

(Continued)

FOREIGN PATENT DOCUMENTS

DE 196 31 654 A1 2/1998

OTHER PUBLICATIONS

International Search Report for PCT/FR2005/000590 dated Jul. 6, 2005.

(Continued)

*Primary Examiner*—David A Vanore
*Assistant Examiner*—Nicole Ippolito Rausch
(74) *Attorney, Agent, or Firm*—Sughrue Mion, PLLC

(57) ABSTRACT

The invention relates to a method of determining the consumption of oil from an oil separation system (2) in the blow by gas recycling circuit of an internal combustion engine. The invention is characterised in that it comprises the following steps consisting in: marking the lubrication oil of the engine by inserting at least one radioactive tracer, trapping the oil that has not been separated from the blow by gases exiting the oil separation system (2) in an oil trapping device (4) which is located downstream of the oil separation system (2); using a detector (3), which is positioned close to the oil-trapping device (4) and which is sensitive in the ionising radiation emitted by the radioactive tracer(s), in order to measure the radioactivity of the oil which has not been separated in the oil separation system (2) and which is held back by the oil-trapping device (4); and transmitting the results of said measurements to a computer (5) which can calculate therefrom the consumption of lubricating oil that has not been separated in the separation system (2). The invention also relates to a device for implementing one such method.

17 Claims, 6 Drawing Sheets

U.S. PATENT DOCUMENTS

| | | | |
|---|---|---|---|
| 2,957,986 A | | 10/1960 | Quigg |
| 3,471,696 A | * | 10/1969 | Moore et al. ............... 250/303 |
| 4,048,497 A | * | 9/1977 | Fritzsche ................... 250/303 |
| 6,294,389 B1 | * | 9/2001 | Vitale et al. ................. 436/57 |
| 7,291,836 B2 | * | 11/2007 | Delvigne et al. ............ 250/303 |
| 2002/0129586 A1 | * | 9/2002 | Tanaka ....................... 55/320 |

FOREIGN PATENT DOCUMENTS

| | | |
|---|---|---|
| GB | 1095056 A | 12/1967 |
| WO | WO98/05854 * | 2/1998 |

OTHER PUBLICATIONS

K. Jost, "Radioactive Measurement Techniques for Engine Testing", Automotive Engineering, Society of Automotive Engineers, Mar. 1, 1996, pp. 33, vol. 104, No. 3.

International Search Report for PCT/FR05/000590 dated Jul. 6, 2005.

M. Bergmann, et al., "Method Zur Oelverbrauchsmessung Durch Markierung Mit Radioaktivem Brom", MTZ Motortechnische Zeitschrift, Franckh'Sche Verlagshandlung, Abteilung Technik, Feb. 1, 1997, pp. 102-107, vol. 58, No. 2.

* cited by examiner

METHOD AND DEVICE FOR THE REAL-TIME MEASUREMENT OF THE CONSUMPTION OF OIL FROM AN ENGINE OIL SEPARATION SYSTEM, USING RADIOACTIVE TRACERS

The present invention relates to a method of measuring, in real time, the consumption of engine oil owing to the flow of crankcase gases, called hereafter blowby gases through the oil separation system for separating the oil contained in said blowby gases.

This oil separation system generally consists of at least one separator, which may in particular take the form of a single separator or several separators connected in series and/or in parallel, and constitutes the principal component of the circuit for recycling the blowby gases within internal combustion engines.

The invention also relates to a device, such as a test bed, for implementing this method. More precisely, this method is based on the real-time measurement of the fraction of engine oil contained in the blowby gases after they pass through the oil separation system of an internal combustion engine.

The blowby gases result largely from the leakage of the combustion gases from the engine block, and more particularly from the combustion chamber, these leaks being due to the mechanical clearances in what is commonly referred to as the PRC (piston(s), ring(s), cylinder(s)) region (a phenomenon called "blow-by"). These blowby gases contain combustion products, engine oil, unburnt hydrocarbons, particles, water vapor, etc.

For many years, in internal combustion engines the blowby gases coming from the engine block, that is to say especially from the cylinder crankcase and/or cylinder head, were treated so as to be subsequently either released into the atmosphere (for example in the case of heavy-duty truck engines) or recycled into the intake and sent back to the cylinders, to be burnt therein (for example in the case of light-duty vehicle engines).

This recycling of the blowby gases into the intake system generally comprises:
(a) a step of recovering the engine oil contained in the blowby gases, this oil being in the form of a multiphase liquid/vapor mixture, the proportions of which vary according to the operating conditions of the engine (e.g. engine load, temperature, pressure);
(b) a step of returning the recovered oil to the engine oil sump; and then
(c) a step of returning the de-oiled blowby gases to the intake or of releasing the de-oiled blowby gases into the atmosphere.

Step (a) of separating the oil from the blowby gases takes place in a separation system, usually called the "engine separator". For this purpose, many technological variations of separation systems have been developed. For example, the oil may be retained by a large contact area provided by static elements, such as baffles or packing elements, or filtering elements, or the oil may be retained through the centrifugal force of one or more cyclones that throw the droplets against the surface of the separator.

However, in general such separators are not completely effective, that is to say a relatively large fraction of the oil contained in the blowby gases is not retained within the separation system. Consequently, returning the blowby gases still containing oil after passing through the separation system to the intake results in a number of technical problems liable to impede the proper operation of the internal combustion engine.

Thus, the risks of fouling the engine are substantially increased. For example, fouling of the intake nozzles, butterfly valves, EGR and other valves, and combustion chambers may be observed. The risks of disruptive mechanical effects, such as seizing of the butterfly valve(s), seizing of the EGR valve or valves, pinging, etc. are consequently increased.

Furthermore, engine fouling is liable to increase the polluting emissions (e.g. incomplete combustion of the oil with possible implications for the post-treatment systems) and to have a not insignificant impact on the agreeableness of driving of the motor vehicle.

Consequently, automobile manufacturers with a concern for developing new oil separation systems comprising one or more separators in series and/or in parallel must be capable of monitoring their performance easily and effectively. Such monitoring requires a method of measuring the oil consumption of said separation system that has to be reliable, precise, repeatable and reproducible.

To evaluate this oil consumption within the separation system, it is necessary to measure the fraction of oil still present in the blowby gases after said gases have passed through this separation system. The more effective the separation system, the lower the measured oil fraction.

For this purpose, the Applicant has developed a novel method of measuring the consumption of oil coming from the oil separation system located in the circuit for recycling the blowby gases of an internal combustion engine, which method is implemented in an easy, automatable, reliable, precise, repeatable and reproducible manner and can operate continuously so as to provide, almost instantaneously and in real time, the fraction of oil not recovered by the separation system.

The method according to the invention thus makes it easier to carry out trials for the purpose of developing new separation systems for optimum de-oiling of the blowby gases.

The method of analysis of the present invention is based on introducing a radioactive tracer into the engine lubricating oil and on measuring the radioactivity of the oil contained in the blowby gases coming from the separation system, which consists of one or more oil separators whose efficiency it is desired to evaluate.

Provided that certain conditions relating to the choice of radiotracer are respected, this radioactivity perfectly reflects the fraction of lubricating oil still contained in the blowby gases after they have passed through the separation system. Thus, by measuring this radioactivity, it is possible to determine in real time the effectiveness of the separation system.

One subject of the present invention is therefore a method of determining the consumption of oil coming from the oil separation system located in the circuit for recycling the blowby gases of an internal combustion engine, characterized in that:
the lubricating oil for said engine is labeled by introducing at least one radioactive tracer into said oil;
the blowby gases, leaving the engine block and laden with lubricating oil, are made to pass through an oil separation system where at least some of the oil contained within said gases is separated, collected and returned to the oil sump, preferably directly into the oil contained in said oil sump;
the radioactivity of the oil not separated in the oil separation system and contained in the blowby gases leaving said separation system is measured using a detector, which is sensitive to the ionizing radiation emitted by the radioactive tracer(s); and the results of these measurements are sent to a computer capable of calculating the consumption of lubricating oil not separated in said separation system from these results.

The oil consumption may be expressed in various forms, depending on the type of test carried out. In particular, it may be expressed:

by weight (in grams);
by volume (in liters);
by weight per unit time (mass flow rate, for example in grams/hour);
by volume per unit time (volume flow rate, for example liters/hour);
in weight per unit distance traveled by the vehicle (for example grams/km); or
by volume per unit distance traveled by the vehicle (e.g. in liters/km).

Another subject of the invention is a device for implementing the above method, which comprises:

an internal combustion engine lubricated by an oil labeled by introducing at least one radioactive tracer into said oil;
an oil separation system that receives the blowby gases laden with lubricating oil leaving the engine block, where at least some of the oil contained in said blowby gases is separated, collected and returned to the oil sump;
a detector sensitive to the ionizing radiation emitted by the radioactive tracer(s), located downstream of the oil separation system, so as to measure the radioactivity of the oil not separated in the oil separation system but contained in the blowby gases leaving said separation system; and
connected to said detector, a computer programmed for calculating the consumption of lubricating oil not separated in said separation system from the results of the radioactivity measurements.

The method and the device of the present invention provides great measurement flexibility and precision, and also makes it possible, thanks to their great sensitivity, for the oil consumption by the blowby gas separation system to be measured rapidly and almost instantly. They also have the advantage of not disturbing the operation of the engine under test and thus allow good extrapolation of the test results to the actual operating conditions of the engine.

In a first embodiment of implementing the present invention, the residual fraction of radioactive oil contained in the partially de-oiled blowby gases after they have passed through the separation system is measured directly using a detector located close to the outlet pipe of the oil separation system to be tested.

This method of implementation, in which small amounts of radioactivity are measured, may involve the use of radio tracers having a high specific activity or else the use of high concentrations of radio tracers of moderate activity. In such a case, it is of course essential to take appropriate protective measures, allowing the impact of the radioactivity on the environment to be limited.

However, if the detector used has a high sensitivity, the specific activity or the amount of radio tracers used does not necessarily have to be very high.

This measurement method has the advantage of not disturbing the operation of the engine, as it does not in any way modify the fluid flow in the blowby gas recycling circuit.

A second method of implementing the present invention consists in measuring the increase in radioactivity due to the build-up of radioactive oil in a suitable trapping device. Specifically, in this second method of implementation, the residual oil from the partially de-oiled blowby gases coming from the oil separation system are trapped in an oil trapping device located downstream of said oil separation system and the overall radioactivity of the oil thus collected is measured.

The addition of an oil trapping device in the blowby gas recycling circuit is liable to modify the fluid flow in said circuit. Good extrapolation of the test results to the actual operating conditions consequently means minimizing such a potential disturbance, by choosing a suitable geometry for this trapping device (small volume, minimal length of the lines, etc.). The parameter best reflecting the disturbance of the fluid flow in the blowby gas recycling circuit is the blowby gas pressure difference ($\Delta P$) between the inlet and outlet of the oil separation system. When the value of this parameter is substantially the same as the pressure difference in the absence of the trapping device, there is no disturbance of the fluid flow by the device, which corresponds to a preferred method of implementation.

This second method of implementation using a trapping device has the considerable advantage of allowing very accurate measurements using low concentrations of radio tracers or using radio tracers of relatively low activity, which are therefore easy to use and entail no risk to the environment or to the operators carrying out the trials.

The abovementioned oil trapping device preferably consists of at least one separator operating according to the same principle as the oil separation system to be tested. The oil trapping device of the present invention comprises, for example, one or more static separation elements, such as baffles or packing elements, providing a large solid/gas interface, and/or filtering elements and/or one or more cyclones for capturing the oil due to the centrifugal force.

Under certain operating conditions of the engine, it may be useful to cool the oil trapping device by means of a suitable cooling system so as to improve the trapping effectiveness of this device.

Furthermore, it will be understood that the more effective the trapping device and the more closely it tends toward 100% efficiency, the more the measurement of the radioactivity of the oil accumulated in the trapping device correctly reflects the oil consumption by the engine separation system. In particular, there are trapping devices that retain most, that is to say at least 80% or ideally at least 95%, of the fraction of oil contained in the blowby gases leaving the engine separation system. However, it is also possible for the oil consumption due to the passage of the blowby gases through the oil separation system to be reliably and reproducibly measured using trapping devices of lower efficiency preestablished by calibration, provided in particular that the ratio of the amount of trapped oil to the amount of incoming oil is known, and that this ratio is known for the various experimental conditions used.

The method of measuring the engine oil consumption due to the blowby gases passing through the oil separation system of an internal combustion engine must be implemented with a suitable radioactive tracer. In particular, the latter must meet the conditions indicated in the following paragraphs.

The radio tracer must not disturb the operation of the engine or upset the physico-chemical properties of the engine oil. To do this, it must in particular be chemically inert with respect to the components of said oil, must have a function similar to that of one of their constituents (for example a functional additive), and must be partly or completely substituted therefor.

The radio tracer must have sufficient radioactivity to allow precise and reproducible measurements. The choice of radio tracer is linked in particular to the sensitivity of the detector used. In other words, if the detector is of low sensitivity, the radioactivity of the oil must be high (high radioactivity of the radio tracer or high concentration of a radio tracer of relatively low radioactivity). However, if the detector used has a high sensitivity, the radioactivity of the oil may be relatively lower.

Finally, the radio tracer must be selected so that the amount of it in circulation in the engine oil circuit, over the entire duration of the method, is directly proportional to the amount of lubricating oil in the engine oil circuit.

This proportionality depends on the physico-chemical properties of the radioactive tracer and of those of the liquid medium into which it is initially introduced. This is because, to reflect at any moment the measured fraction of engine oil, the radioactive tracer must neither be accumulated in the mixture when the oil is consumed nor must it be consumed more rapidly than the latter, for example by evaporation, combustion or thermal decomposition, nor must it be trapped at any point in the engine, such as the oil filter.

In light of the foregoing, a person skilled in the art will choose the radio tracer so that its physico-chemical properties (volatility, thermostability, chemical reactivity) are matched with those of the liquid medium into which it is introduced and of which it must reflect the measured fraction.

A person skilled in the art may in particular find a suitable tracer for a given medium by subjecting a tracer/lubricating oil mixture to the temperature and pressure conditions prevailing in an engine.

The detectors that can be used are probes for detecting ionizing radiation ($\beta$-rays, X-rays or $\gamma$-rays) which may either be of the liquid or solid scintillator type (sodium iodide NaI (Tl) crystal or BGO crystal) or of the semiconductor type (germanium crystal, or CZT crystal). It should also be noted that the detector may detect the simultaneous presence of various radio tracers. When the radioactivity of the oil contained in the blowby gases is high (highly radioactive radio tracer and/or high concentration of a radio tracer of low radioactivity), the detector will not need to be of high sensitivity. However, when the radioactivity of the oil contained in the blowby gases is not high, the detector will have to have a higher sensitivity.

To limit the amount of radio tracers employed, it will be preferred to use a measurement probe of high detection efficiency, for example a crystal of the sodium iodide type measuring 3×3 inches.

This type of detector may exist in compact form, allowing the possibility of a device on board the vehicle.

The signals detected by the detector are then processed by a series of means for calculating the fraction of engine oil contained in the blowby gases after they have passed through the oil separation system. These means comprise in particular a means of processing the detected signal (for example an amplifier, a filter and an ADC (analog/digital converter)), a pulse processing means (for example a multichannel analyzer) and a means of storing and processing the data acquired (for example a PC computer).

The measurement of the radioactivity and the processing of the results are preferably carried out continuously.

The radioactive tracer that can be used in the present invention may either be an organic or mineral compound of a radioactive element (radionuclide) or the radioactive element itself, which is then in elemental form. However, on account of the above considerations regarding the physico-chemical properties of the radioactive tracer relative to those of the lubricating oil, the organic or mineral molecular forms of radiotracers are preferred over the elemental forms of the radionuclides.

The radio tracer is therefore chosen from organic or mineral compounds or elements meeting the abovementioned conditions (i.e. inertness with respect to the lubricant or substitution for one of the components of the lubricant, sufficient radioactivity, oil/tracer proportionality). However, for obvious handling and environmental protection reasons, it will be preferred to choose tracers containing radionuclides having a short period, or half-life, preferably a period of less than 3 years, in particular less than 1 year and even more preferably less than 30 days. In this way, the production of radioactive waste of long half-life is avoided.

It is preferable that the period of the radionuclide be at least as long as the planned duration of the trial. The computer, thanks to the law of radioactive decay will be easily able to correct the measured value.

Examples of radionuclides of suitable period that may be mentioned include the following (the period being indicated in parentheses): $^{22}$Na (2.61 years), $^{65}$Zn (243.8 days), $^{45}$Ca (165 days), $^{35}$S (87.2 days), $^{32}$P (14.3 days), $^{47}$Ca (4.54 days), $^{99}$Mo (65.9 hours), $^{82}$Br (35.3 hours), $^{64}$Cu (12.7 hours), $^{99M}$Tc (6.01 hours), $^{28}$Mg (20.91 hours), $^{68}$Ge (270.95 days), $^{69}$Ge (39 hours), $^{77}$Ge (11.30 hours), $^{85}$Sr (64.8 days) and $^{56}$Co (77.3 days).

These radio tracers are in general produced artificially by nuclear reactions, especially by activation reactions. This activation is accomplished using methods familiar to those skilled in the art, for example by exposing inactive elements or compounds containing said inactive elements to a source of neutron radiation, or else by exposing them to a beam of accelerated ions coming from a particle accelerator.

Depending on the case, the inactive elements or compounds containing said inactive elements are activated either before their incorporation into the engine oil, or are activated within the oil, that is to say by exposing the oil containing the element or compound that can be activated to, for example, neutron radiation or to a proton beam.

One of the possible options for obtaining artificial radionuclides is to incorporate the inactive elements or compounds containing said inactive elements in a suitable amount of a carrier (for example a solvent or diluent, such as an oil), then in subjecting this mixture to the activation process and finally to add it to the lubricating oil.

The radio tracers may be additives normally used in lubricating oils, such as corrosion inhibitors, antioxidants, viscosity modifiers, lubricating additives, dyes, pour point reducers, detergents or dispersants. As examples of such radio tracers operating as a functional additive, mention may be made of: zinc dithiophosphate, calcium or magnesium sulfonates, such as calcium or magnesium alkylsulfonates, arylsulfonates or alkylarylsulfonates; calcium phenates, magnesium phenates, calcium salicylates; and magnesium salicylates.

However, the use of radio tracers that do not have any physical or chemical function in the engine lubrication system are just as suitable.

The Applicant has found that particularly useful radioactive tracers for introduction into the engine oil are certain compounds of germanium 69. These compounds are chosen for example from tetraalkylgermanes. Since the boiling point of these tetraalkylgermanes is proportional to the length of the alkyl chains, it will be advantageous to use a mixture of tetraalkylgermanes having alkyl chains such that the boiling point of the mixture lies within the distillation range of the oil used. For example, tetrahexylgermane, tetraheptylgermane and tetraoctylgermane each have a boiling point similar to that of a conventional engine lubricant.

Another particularly useful radio tracer, in particular because of its ease of preparation and handling, and because of its very short lifetime, is $^{99m}Tc$, preferably in the form of an aqueous solution of sodium pertechnetate $NaTcO_4$ or in the form of nanoscale particles isolated from the atmosphere by carbon.

The invention will now be described with reference to the appended nonlimiting drawings in which.

Figure 4:
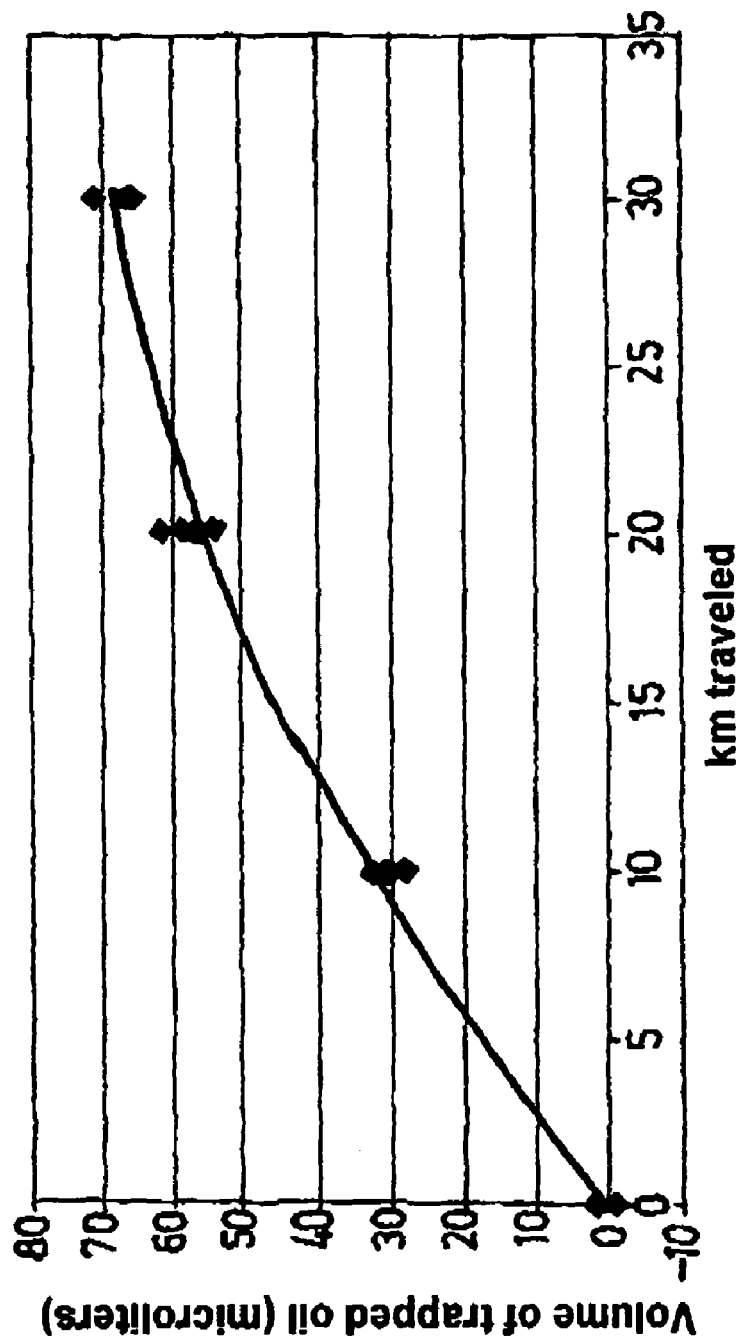
Figure 5:
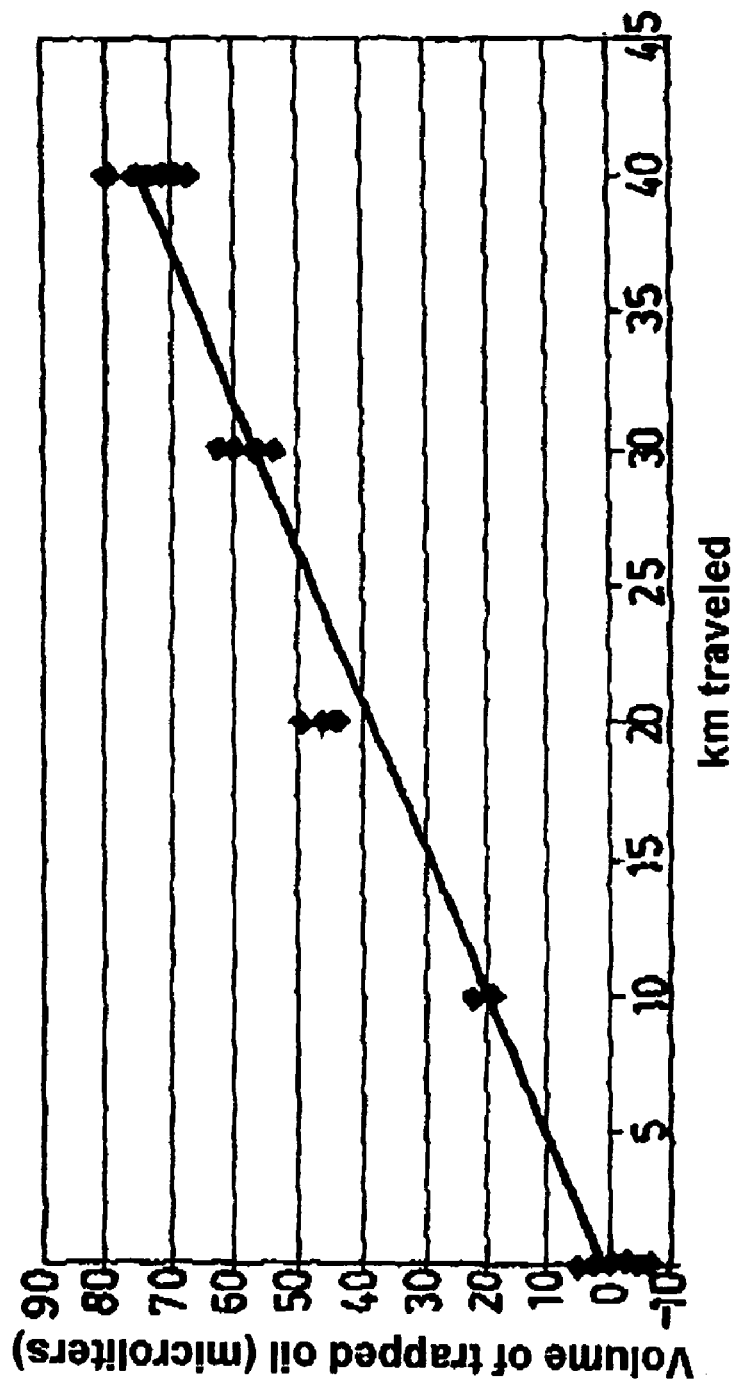

FIG. 4 is a graph showing the amount of oil trapped in a first trapping device, placed downstream of an oil separation system of a circuit for recycling the blowby gases of an internal combustion engine, as a function of the number of kilometers traveled by the vehicle; and FIG. 5 is a graph showing the amount of oil trapped in a second trapping device, placed downstream of an oil separation system of a circuit for recycling the blowby gases of an internal combustion engine, as a function of the number of kilometers traveled by the vehicle.

Figure 6:
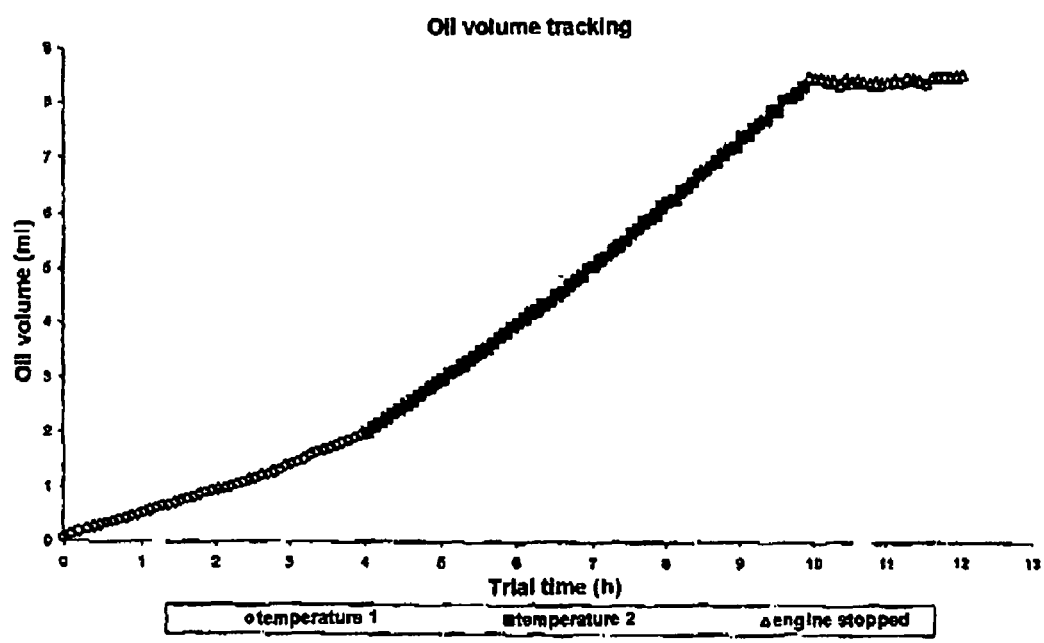

FIG. 6 is a graph showing the amount of oil trapped in a trapping device located downstream of an oil separation system as a function of the number of hours of the trial, according to Example 3.

Figure 1:
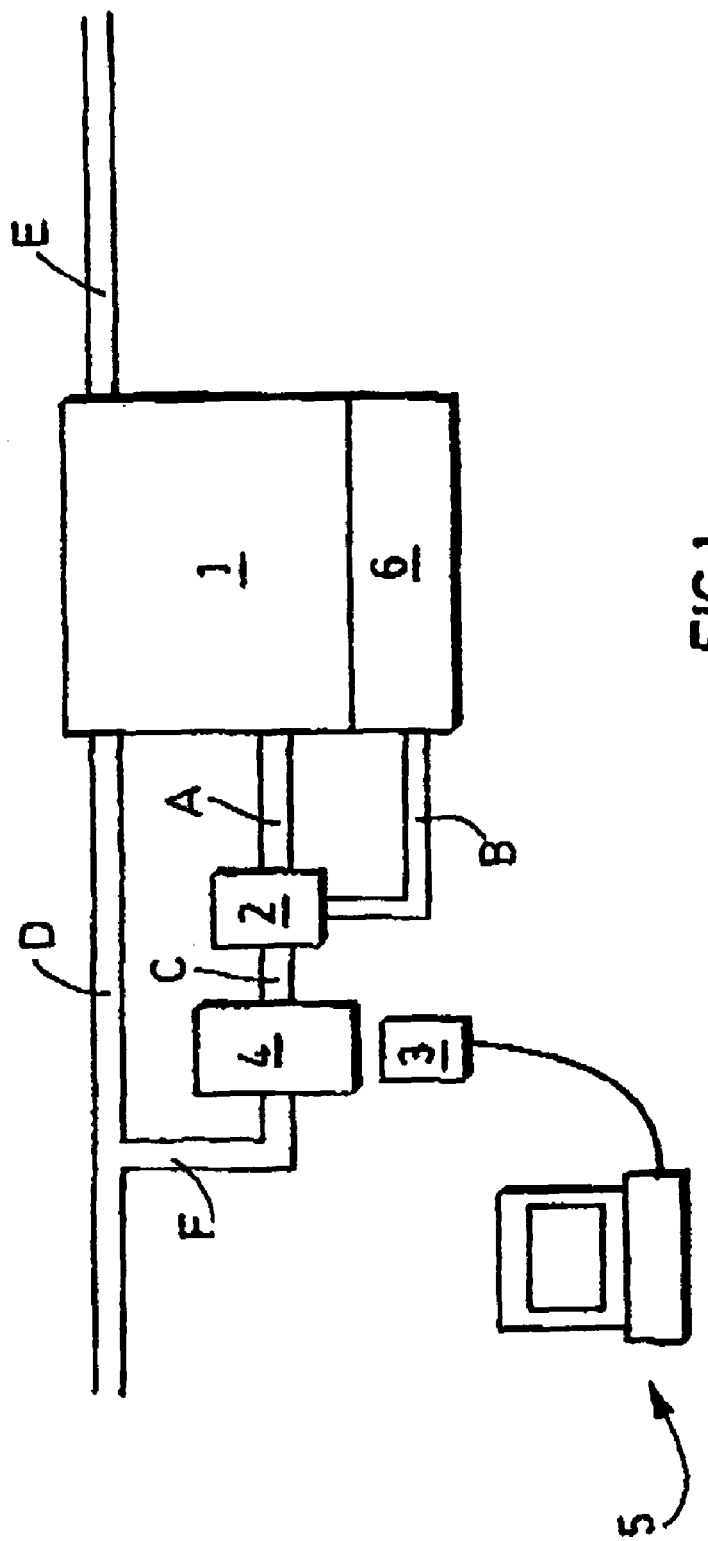
FIG. 1 shows a first version of the method of measuring the oil consumption according to the invention, in which the radioactive oil contained in the blowby gases leaving the oil separation system is trapped in a trapping device.
Figure 2:
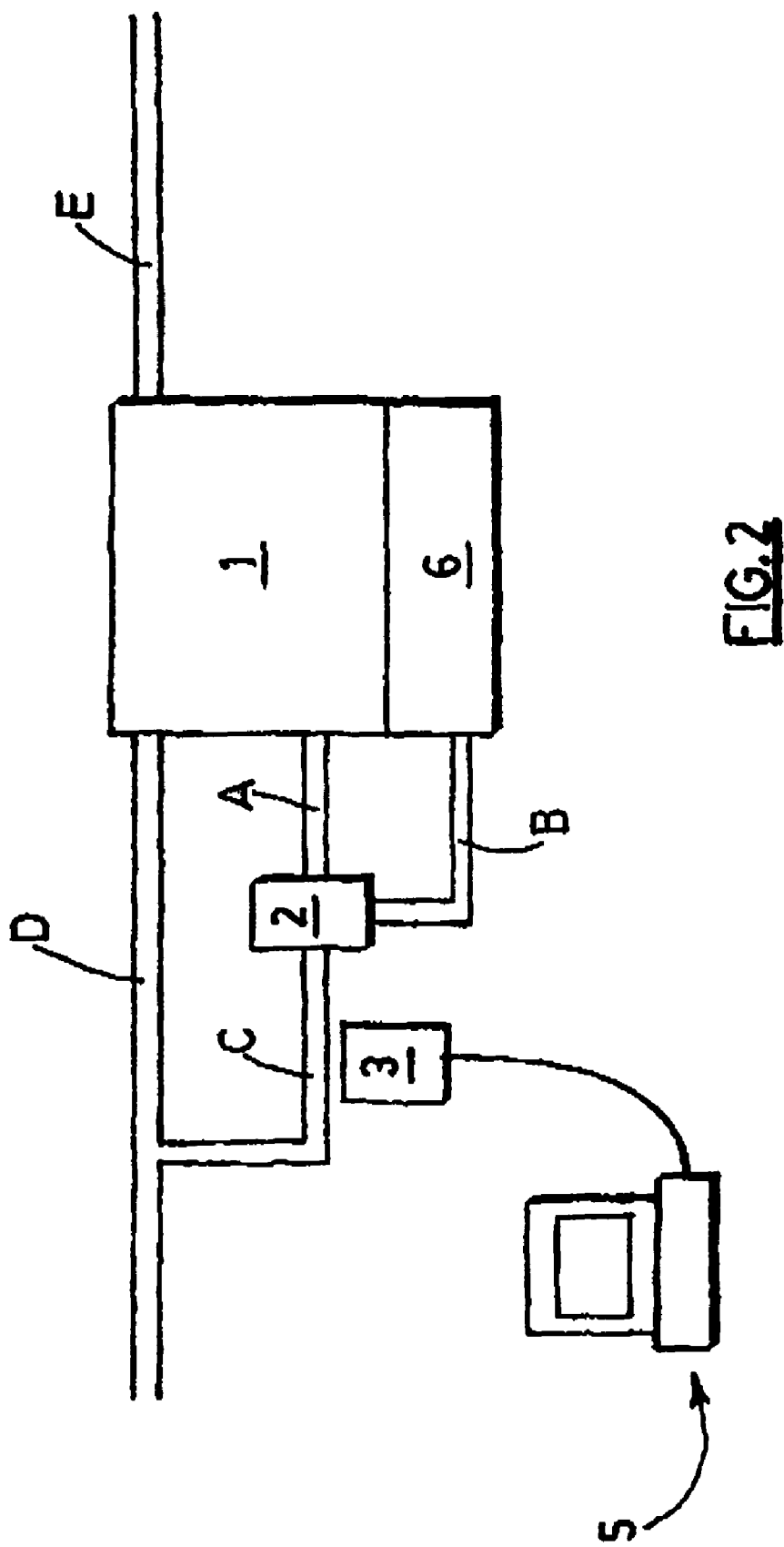
FIG. 2 shows a second version of the method of measuring the oil consumption according to the invention, in which the radioactivity of the radioactive oil contained in the blowby gases leaving the oil separation system are measured directly, without prior trapping of the oil.
Figure 3:
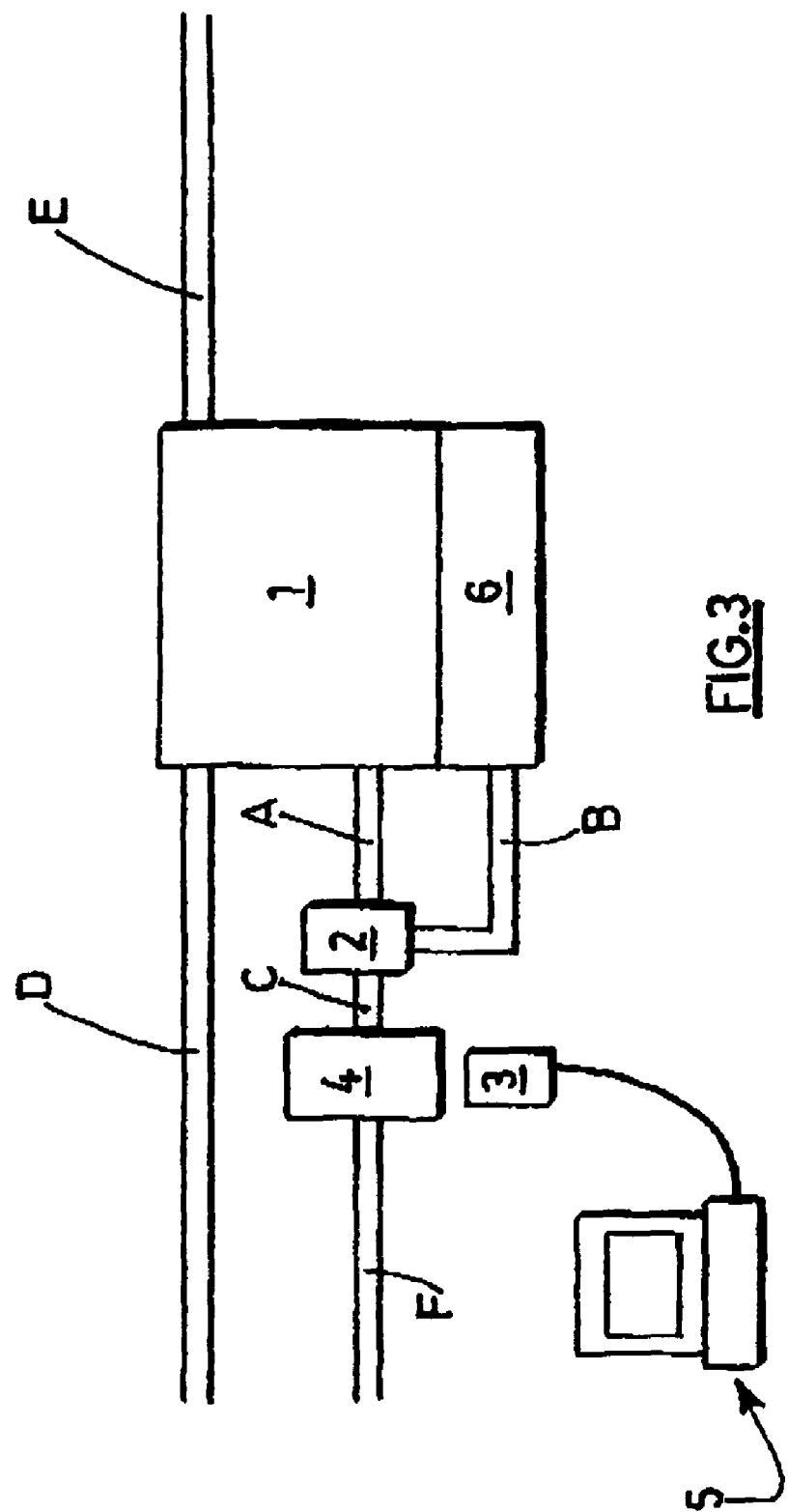
FIG. 3 shows a third version of the method of measuring the oil consumption according to the invention, which differs from the method of FIG. 1 by the fact that the treated blowby gases are not returned to the intake but released into the atmosphere.

In all the diagrams shown in FIGS. 1 to 3, the oil separation system is illustrated in the form of a single separator. If the separation system comprises two or more separators connected in series, a direct measurement may be made at the outlet of each separator. Alternatively, a single measurement may be made at the outlet of the separator furthest downstream, with or without trapping of the oil by a trapping device, in order to calculate the overall consumption of the system.

The internal combustion engine may also include several separation systems connected in parallel (for example a V6 engine). In this case, the consumption may be measured either on all of the blowby gases brought together downstream of the separation systems, with or without trapping of the oil, or at the outlet of each separation system (each possibly also comprising several separators) when the blowby gases coming from each separation system are not brought together in a single line but are sent separately to the intake or into the atmosphere.

The invention will now be described with reference to FIG. 1. In this embodiment, the blowby gases laden with oil labeled by at least one radioactive tracer leave the engine block 1 and enter, via the inlet line A, the oil separator 2. The separation of the oil contained in these blowby gases takes place in this oil separator 2. The oil thus separated is sent into the oil sump 6 via the return line B.

The imperfectly de-oiled blowby gases, which still contain a certain fraction of radioactive oil, are sent via the outlet line C to the oil trapping device 4 where the residual oil is retained.

The blowby gases, now completely or almost completely de-oiled, are returned to the intake D via the line F.

A detector 3, sensitive to the radiation emitted by the radio tracer(s) introduced into the lubricating oil, is placed in the immediate vicinity of the trapping device 4 containing the separated oil. This detector must be protected by a suitable material, for example lead, from the radiation emitted by the radioactive lubricating oil in circulation in the engine located nearby. The detector 3, thus protected against this parasitic radiation, measures only the radioactivity that has built up in the trapping device 4.

The detector 3 is connected to a computer system 5 for recording and processing the measurement data, and is programmed to calculate the oil consumption by the oil separation system 2 in the blowby gas recycling system.

The method of FIG. 2 differs from that shown in FIG. 1 by the fact that the blowby gases leaving via the outlet line C of the oil separation system 2 are recycled directly into the intake. The measurement of the radioactivity by the detector 3 connected to the computing system 5 takes place without prior trapping of the residual oil present in the blowby gases coming from the separation system 2. The detector 3 is placed close to the line C where it measures the radioactivity of the blowby gas flow in this line. This embodiment, unlike that of FIG. 1, is completely non-intrusive, that is to say it does not involve any modification of the flow of the gases in the engine and in the blowby gas recycling system.

Finally, the method shown in FIG. 3 is substantially identical to that of FIG. 1, except that the treated (de-oiled) blowby gases are not recycled to the intake D but released into the atmosphere.

The invention will be more clearly understood on reading the following examples, which are purely illustrative and in no way limit the scope of the present invention.

EXAMPLES

These examples constitute trial configurations. They are intended to illustrate the method of measuring, in real time, the consumption of engine oil due to the blowby gases passing through the system for separating the oil contained in said gases.

The engine used in these trials was an "F3R" 4-cylinder/8-valve petrol engine of 2 liter capacity, fitted to a Renault Espace vehicle.

The 4-stroke engine oil was an oil sold under the ELF brand, of the Evolution SXR 5W30 type.

As radioactive tracer, germanium 69, prepared in the form of a complex of tetraalkylgermanes soluble in the oil, and the distillation range of which was representative of the lubricant, was used. The total activity employed was 37 MBq (1 mCi), the tracer being mixed with five liters of engine sump oil.

The oil trap used was fitted close to the engine, between the outlet of the oil separator and the return to the intake manifold.

Two types of traps were used, corresponding to the two examples below. In the case of Example 1, the cartridge used contained a resin-impregnated high-density animal wool (filter wool sold by Vita Medical Ltd., Australia). The trap used for Example 2 consisted of stainless steel filings (fine entangled spirals). The total volume of each type of trap was around 100 ml.

The trials were carried out under identical and repeatable conditions (3 km on a road+7 km on a freeway, gear changes at similar engine speeds, same average freeway speed, etc.).

After each run, the vehicle was returned to the workshop and a radioactivity measurement probe was repositioned in an identical manner close to the trap so as to determine the fraction of oil built up in the filter, via a gamma-radiation measurement (511 keV line).

Precautions were taken to focus the measurement probe on the radiation emitted by the trap, while minimizing the impact of the signal coming from the oil contained in the engine. A lead shield was used for this purpose and the probe was positioned against the trap, but as far as possible from the engine block.

Several measurement points were effected after each run, the count time being 30 seconds per measurement point.

The radiation detection system consisted of a standard 3×3 inch NaI(Tl) detector with an integrated photomultiplier tube, the other elements of the measurement chain being a 2007P model charge preamplifier of the Canberra brand, a 2020 spectroscopy amplifier (from Canberra) an 8087 model ADC converter (from Canberra) and an S100 model multichannel card (from Canberra).

The software used during these trials was "Genie 2000" (from Canberra) for gamma spectroscopy, and also the MCS (Multi Channel Scaling) analysis software called "IDSWear" sold by Atlantic Nuclear Services (ANS), Canada. The results presented below include a half-life correction (the half-life being 39 hours in the case of $^{69}$Ge) by the "IDSWear" measurement software.

It should be noted that the procedure applied here was of the almost continuous type, that is to say each measurement point was at a regular and identical time and distance interval.

Example 1

The graph of FIG. 4 shows the amount of oil trapped in a trapping device located downstream of an oil separation system as a function of the number of km traveled by the vehicle.

The volume of trapped oil was calculated on the basis of the specific activity of the engine oil (which was 7.4 Bq per microliter at the start of the trial), taking into account the efficiency of the detector and the detection geometry.

The overall efficiency (about 7%) on the 511 kev peak was evaluated via a computation code of the "Monte Carlo" type, the input parameters of which were adapted to the measurement configuration.

The increase in activity detected as a function of time was thus directly converted into the volume of oil trapped. It may be seen in the graph that the trapped volume does not increase linearly with the number of km traveled.

This result is explained by the fact that the impregnated wool contained in the trap is also very effective at trapping water vapor. The wool is therefore impregnated little by little with water, this having the consequence that it becomes increasingly difficult for the gases to flow into the trap, and therefore that the volume of trapped oil per km traveled decreases with time.

Nevertheless, it may be seen that, at the start of the trial, there is an oil consumption of about 3 microliters per km traveled.

Example 2

FIG. 5 is a graph showing the amount of oil trapped in a trapping device containing stainless steel filings, located downstream of an oil separation system, as a function of the number of km traveled.

The volume of trapped oil was calculated on the basis of the specific activity of the engine oil (which was 5.48 Bq per microliter at the start of the trial), taking into account the efficiency of the detector and the detection geometry.

The overall efficiency (about 7%) on the 511 keV peak was evaluated via a computation code of the "Monte Carlo" type, the input parameters of which were adapted to the measurement configuration.

The increase in activity detected as a function of time was thus directly converted into the volume of oil trapped. It may be seen in the graph that the trapped volume increases almost linearly with the number of km traveled.

The deviation from the regression line noted for the third series of measurements carried out at 20 km is explained by the traffic conditions, which were slightly varied.

The good linearity of the curve obtained is explained by the fact that the material used here has no tendency to accumulate the water contained in the blowby gases. Consequently, the resistance of the trap to the flow of gases does not vary with time.

The average oil consumption recorded was 1.875 microliters per km traveled, a lower value than that recorded in Example 1. This is explained by a considerably coarser mesh in the case of the stainless steel filter, which does not trap all the residual oil leaving the oil separation system.

Example 3

This example is intended to illustrate the method of real-time measurement of the engine oil consumption due to the blowby gases passing through the system for separating the oil contained in said gases.

The engine used in this trial was an "L7X" 6-cylinder/24 valve petrol engine, of 3 liter capacity, fitted on an engine test bed.

The 4-stroke engine oil was an oil sold under the TOTAL brand, of LUB MA3 5W-30 type.

The radioactive tracer used was $^{99}$Tc (gamma-radiation at 141 keV), prepared in the form of a mixture of the abovementioned oil and carbon nanoparticles containing $^{99}$Tc. The specific activity of the oil/$^{99}$Tc mixture used in this trial was 2 kBq/ml (2.3 kBq/g), i.e. a total activity in the engine of about 14,000 kBq.

The oil trap used was fitted close to the engine, between the outlet of the oil separator and the return to the intake manifold. This trap was of the cyclone type with a volume of around 10 ml, giving a pressure drop of less than 10 mbar, which was compensated for by the use of connecting tubes with no pressure drop, so as to guarantee a flow identical to the standard engine system. The oil trapped from the effluents was collected in a flask of 100 ml capacity.

The measurement was made in real time and continuously, the computer being programmed to calculate an average value per 5 minute measurement period. The detection chain remained in the same configuration throughout the trial.

Precautions were taken to focus the measurement probe on the radiation emitted by the trap, while minimizing the impact of the signal coming from the oil contained in the engine. A thick lead shield was used for this purpose, and the probe was positioned against the trap as far as possible from the engine block.

The radiation detection system consisted of a standard 2×2 inch NaI (T1) detector with an integrated photomultiplier tube, the other elements of the measurement chain being a 2007P model charge preamplifier of the Canberra brand, a 2020 spectroscopy amplifier (from Canberra), an 8087 model ADC converter (from Canberra) and an S100 model multi-channel card (from Canberra).

The software employed during these trials was "Genie 2000" (from Canberra) for the gamma spectroscopy, and also the MCS (Multi Channel Scaling) analysis software called "IDSWear" sold by Atlantic Nuclear Services (ANS), Canada. The results presented below include a half-life correction (the half-life being 6 hours in the case of $^{99}$Tc) by the "IDSWear" measurement software.

The graph of FIG. 6 shows the amount of oil trapped in a trapping device located downstream of an oil separation system as a function of the number of hours of the trial.

The volume of trapped oil was calculated on the basis of the specific activity of the engine oil (which was 2 Bq per microliter at the start of the trial), taking into account the efficiency of the detector and the detection geometry.

The overall efficiency (about 6%) on the 141 keV peak was evaluated on the basis of the volume of trapped oil at the end of the trial.

The increase in detected activity as a function of time can thus be converted into a volume of trapped oil.

During this trial, three phases were implemented: a first phase on an operating point stabilized for regulating an oil temperature 1 lasting 4 hours; a second phase for an oil temperature 2 lasting 6 hours; and, finally, a stopped engine test lasting 2 hours. The graph clearly shows three different slopes depending on the three phases, namely: 37.8 microliters between two measurements points during the first phase; 90.1 microliters between two measurement points during the second phase; and 2.2 microliters between two measurement points during the final phase.

For the last phase, the slight increase is explained essentially by the slight trickling into the trapping device.

The invention claimed is:

1. A method for determining oil consumption coming from an oil separation system located in a circuit for recycling blowby gases of an internal combustion engine, comprising:
    labeling the lubricating oil for said internal combustion engine by introducing at least one radioactive tracer into said lubricating oil;
    passing the blowby gases, leaving the engine block and laden with lubricating oil, through the oil separation system, wherein at least some of the oil contained within said blowby gases is separated, collected and returned to an oil sump;
    subsequently bringing the blowby gases coming from the oil separation system to an oil trapping device located downstream of said oil separation system, whereby the oil not separated from the blowby gases coming from the oil separation system is retained in the oil trapping device;
    measuring the radioactivity of the oil retained in the oil trapping device by using a detector, which is placed near the oil trapping device and is sensitive to the ionizing radiation emitted by the radioactive tracer(s); and
    transmitting the results of these measurements to a computer capable of calculating the consumption of lubricating oil not separated in said separation system from these results.

2. The method as claimed in claim 1, wherein the oil separation system comprises several separators connected in series or in parallel.

3. The method as claimed in claim 1, further comprising releasing the blowby gases coming from the trapping device into the atmosphere or to an intake (D) of the internal combustion engine.

4. The method as claimed claim 1, wherein the oil trapping device is a second separation system comprising one or more static separation elements and/or one or more cyclones and/or one or more filtering elements.

5. The method as claimed in claim 1, wherein the oil trapping device is designed so that the pressure difference ($\Delta P$) between the inlet of the oil separation system and the outlet of the oil separation system is substantially the same as the value of this pressure difference in the absence of the trapping device.

6. The method as claimed in claim 1, wherein the radioactive tracer is an organic or mineral compound of a radioactive element.

7. The method as claimed in claim 1, wherein the radioactive element has a period, or half-life, of less than 3 years.

8. The method as claimed in claim 7, wherein the radioactive element is selected from the group consisting of $^{22}$Na, $^{65}$Zn, $^{45}$Ca, $^{35}$S, $^{32}$P, $^{47}$Ca, $^{99}$Mo, $^{82}$Br, $^{64}$Cu, $^{99m}$TC, $^{28}$Mg, $^{68}$Ge, $^{69}$Ge, $^{77}$Ge, $^{85}$Sr and $^{56}$Co.

9. The method as claimed in claim 8, wherein the radio tracer is selected from the group consisting of tetra-alkylgermanes containing $^{69}$Ge.

10. The method as claimed in claim 8, wherein the radio tracer is $^{99m}$Tc.

11. The method as claimed in claim 8, wherein the radio tracer is selected from the group consisting of tetrahexylgermane, tetraheptylgermane and tetraoctylgermane, and mixtures thereof.

12. The method as claimed in claim 8, wherein the radio tracer is $^{99m}$Tc in the form of an aqueous solution of sodium pertechnetate NaTcO$_4$ or in the form of nanoscale particles isolated from the atmosphere by carbon.

13. The method as claimed in claim 1 wherein the detector is an ionizing radiation detection probe.

14. The method as claimed in claim 1, wherein the radioactive element has a period, or half-life, of less than 1 year.

15. The method as claimed in claim 1, wherein the radioactive element has a period, or half-life, of less than 30 days.

16. A device for determining the consumption of oil coming from an oil separation system located in a circuit for recycling blowby gases of an internal combustion engine, comprising:
    an internal combustion engine lubricated by an oil labeled by introducing at least one radioactive tracer into said oil;
    an oil separation system that receives the blowby gases laden with lubricating oil leaving the engine block, where at least some of the oil contained in said blowby gases is separated, collected and returned to the oil sump;
    downstream of the oil separation system, an oil trapping device;
    a detector sensitive to the ionizing radiation emitted by the radioactive tracer(s), located in the immediate vicinity of the trapping device, so as to measure the radioactivity of the oil not Separated in the oil separation system but retained in the oil trapping device; and
    connected to said detector, a computer programmed for calculating the consumption of lubricating oil not separated in said separation system from the results of the radioactivity measurements.

17. The device as claimed in claim 16, characterized in that the oil trapping device is designed in such a way that the pressure difference ($\Delta P$) between the inlet and the outlet of the oil separation system is approximately the same as the value of this pressure difference in the absence of said oil trapping device.

* * * * *